US010051670B2

(12) United States Patent
Zhang

(10) Patent No.: US 10,051,670 B2
(45) Date of Patent: Aug. 14, 2018

(54) HUMAN PROXIMITY DETECTION TECHNIQUES FOR WIRELESS COMMUNICATION DEVICES

(71) Applicant: INTEL CORPORATION, Santa Clara, CA (US)

(72) Inventor: Guoqing Zhang, Tampere (FI)

(73) Assignee: INTEL CORPORATION, Santa Clara, CA (US)

(*) Notice: Subject to any disclaimer, the term of this patent is extended or adjusted under 35 U.S.C. 154(b) by 0 days.

(21) Appl. No.: 15/089,492

(22) Filed: Apr. 2, 2016

(65) Prior Publication Data
US 2017/0290070 A1    Oct. 5, 2017

(51) Int. Cl.
| | |
|---|---|
| *H04W 76/10* | (2018.01) |
| *H04W 52/04* | (2009.01) |
| *A61B 5/024* | (2006.01) |
| *H04W 4/80* | (2018.01) |
| *H04W 52/28* | (2009.01) |
| *A61B 5/00* | (2006.01) |
| *G06F 19/00* | (2018.01) |
| *A61B 5/0205* | (2006.01) |

(52) U.S. Cl.
CPC ........... *H04W 76/10* (2018.02); *A61B 5/0022* (2013.01); *A61B 5/02438* (2013.01); *G06F 19/30* (2013.01); *H04W 4/80* (2018.02); *H04W 52/04* (2013.01); *H04W 52/283* (2013.01); *A61B 5/02055* (2013.01); *A61B 5/681* (2013.01); *A61B 5/6803* (2013.01); *A61B 2560/029* (2013.01)

(58) Field of Classification Search
CPC ..... H04W 76/02; H04W 4/008; H04W 52/04; A61B 5/02438
USPC ..................................................... 340/870.07
See application file for complete search history.

(56) References Cited

U.S. PATENT DOCUMENTS

| | | | |
|---|---|---|---|
| 2004/0154831 A1* | 8/2004 | Seydoux ................... | E21B 7/04 175/24 |
| 2012/0319846 A1* | 12/2012 | Rogers ..................... | G07C 3/00 340/573.1 |
| 2016/0212194 A1* | 7/2016 | Palin ...................... | G06F 3/0484 |

OTHER PUBLICATIONS

Bluetooth® DOC, Link Loss Service, LLS Specification, Version 1.0.1, Jul. 14, 2015.*
Bluetooth® DOC, Heart Rate Service, HRD Secification, Version 1.0.0, Jul. 12, 2011.*

* cited by examiner

*Primary Examiner* — Nader Bolourchi

(57) ABSTRACT

Human proximity detection techniques for wireless communication devices are described. In one embodiment, for example, an apparatus may comprise a memory and logic, at least a portion of the logic comprised in circuitry coupled to the memory, the logic to perform a connection establishment procedure to establish a wireless link with a human proximity reporting (HPR) device, identify heart rate information comprised in a human proximity report received from the HPR device via the wireless link, determine an initial HPR state based on the heart rate information, and select an initial operating mode for a feature of a human proximity monitoring (HPM) device based on the initial HPR state. Other embodiments are described and claimed.

16 Claims, 11 Drawing Sheets

| LLS/TPS Behavior | HRS Behavior | HPR State |
|---|---|---|
| LLS alerts Bluetooth connection is made or TPS exposes higher transmit power level than threshold value | HRS exposes heart rate value | Worn HPRD |
| LLS alerts Bluetooth connection is lost or TPS exposes lower transmit power level than threshold value | HRS does not expose heart rate value | Unworn HPRD |
| LLS alerts Bluetooth connection is made or TPS exposes higher transmit power level than threshold value | HRS does not expose heart rate value | U/D HPRD |

| Initial HPR State | Initial Auto-Lock Operating Mode |
|---|---|
| *Worn HPRD* | *human proximity trigger mode* |
| *Unworn HPRD* | *timer trigger mode* |

FIG. 5

| Previous HPR State | Current HPR State | Event |
|---|---|---|
| Unworn HPRD | Worn HPRD | user puts on HPR device |
| Worn HPRD | Unworn HPRD | user takes off HPR device |
| Worn HPRD | U/D HPRD | user wearing HPR device leaves vicinity of HPM device |
| U/D HPRD | Worn HPRD | user wearing HPR device returns to vicinity of HPM device |

| Previous HPR State | Current HPR State | Auto-Lock Behavior |
|---|---|---|
| Unworn HPRD | Worn HPRD | switch from timer trigger mode to human proximity trigger mode |
| Worn HPRD | Unworn HPRD | switch from human proximity trigger mode to timer trigger mode |
| Worn HPRD | U/D HPRD | lock HPM device |
| U/D HPRD | Worn HPRD | unlock HPM device |

HUMAN PROXIMITY DETECTION TECHNIQUES FOR WIRELESS COMMUNICATION DEVICES

TECHNICAL FIELD

Embodiments described herein generally relate to wireless communications between devices in wireless networks.

BACKGROUND

The Bluetooth Low Energy (BLE) Proximity profile (PXP) defines a Proximity Monitor role and a Proximity Reporter role, according to one or both of which a given BLE-capable device may be able to operate. In conjunction with operating according to the Proximity Reporter role, a wireless communication device may provide a second wireless communication device operating in the Proximity Monitor role with proximity information generally indicating the proximity of the Proximity Reporter to the Proximity Monitor. In conjunction with operating according to the Proximity Monitor role, the second wireless communication device may monitor a BLE wireless channel for such proximity information. With respect to a given application, service, or feature, it may be possible to configure the Proximity Monitor to operate in different ways depending on whether the Proximity Reporter is located in the vicinity of the Proximity Monitor.

BRIEF DESCRIPTION OF THE DRAWINGS

FIG. 3 illustrates an embodiment of a state table.

FIG. 4 illustrates an embodiment of an operational mode table.

FIG. 5 illustrates an embodiment of a state transition table.

FIG. 6 illustrates an embodiment of a behavior table.

DETAILED DESCRIPTION

Figure 1:
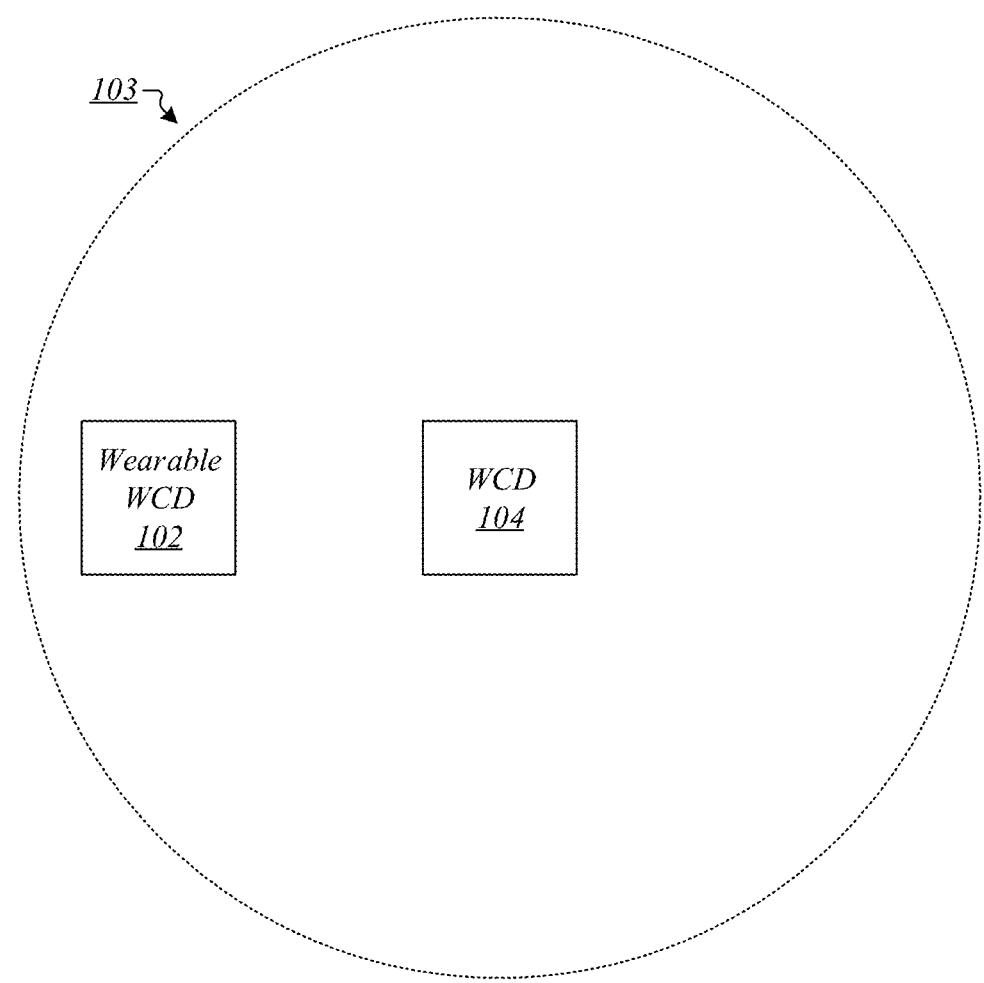
FIG. 1 illustrates an embodiment of a first operating environment.

Various embodiments may be generally directed to human proximity detection techniques for wireless communication devices. In one embodiment, for example, an apparatus may comprise a memory and logic, at least a portion of the logic comprised in circuitry coupled to the memory, the logic to perform a connection establishment procedure to establish a wireless link with a human proximity reporting (HPR) device, identify heart rate information comprised in a human proximity report received from the HPR device via the wireless link, determine an initial HPR state based on the heart rate information, and select an initial operating mode for a feature of a human proximity monitoring (HPM) device based on the initial HPR state. Other embodiments are described and claimed.

Various embodiments may comprise one or more elements. An element may comprise any structure arranged to perform certain operations. Each element may be implemented as hardware, software, or any combination thereof, as desired for a given set of design parameters or performance constraints. Although an embodiment may be described with a limited number of elements in a certain topology by way of example, the embodiment may include more or less elements in alternate topologies as desired for a given implementation. It is worthy to note that any reference to "one embodiment" or "an embodiment" means that a particular feature, structure, or characteristic described in connection with the embodiment is included in at least one embodiment. The appearances of the phrases "in one embodiment," "in some embodiments," and "in various embodiments" in various places in the specification are not necessarily all referring to the same embodiment.

Embodiments herein are generally directed to wireless communications systems. Various embodiments are particularly directed to wireless communications performed according to one or more wireless communications standards. Some such embodiments may involve wireless communications performed according to one or more Bluetooth wireless communication standards. For example, some embodiments may involve wireless communication according to the Bluetooth Core Specification v. 4.2, published Dec. 2, 2014 ("the Bluetooth Core Specification"), and/or one or more predecessors, revisions, progeny, and/or variants. Various such embodiments may involve wireless communications performed according to one or more Bluetooth Low Energy (BLE) protocols and/or techniques. For example, some embodiments may involve wireless communications performed according to one or more protocols and/or techniques defined in Bluetooth Core Specification Vol 6 ("Core System Package [Low Energy Controller volume]"). The embodiments are not limited in this context.

Various embodiments may additionally or alternatively involve wireless communications according to one or more other wireless communication standards. Examples of wireless communications technologies and/or standards that may be used in various embodiments may include—without limitation—Institute of Electrical and Electronics Engineers (IEEE) wireless communication standards such as current, past, and/or upcoming versions of one or more of the IEEE 802.11, IEEE 802.11a, IEEE 802.11b, IEEE 802.11g, IEEE 802.11n, IEEE 802.11u, IEEE 802.11ac, IEEE 802.11ad, IEEE 802.11af, IEEE 802.11ah, IEEE 802.11ax, and IEEE 802.11ay standards, Wi-Fi Alliance (WFA) wireless communication standards such as Wi-Fi, Wi-Fi Direct, Wi-Fi Direct Services, Wireless Gigabit ("WiGig"), WiGig Display Extension (WDE), WiGig Bus Extension (WBE), WiGig Serial Extension (WSE) standards and/or standards developed by the WFA Neighbor Awareness Networking (NAN) Task Group, and/or near-field communication (NFC) standards such as standards developed by the NFC Forum, including any predecessors, revisions, progeny, and/or variants of any of the above.

Some embodiments may involve wireless communications performed according to one or more broadband wireless communication standards. For example, various embodiments may involve wireless communications performed according to one or more 3rd Generation Partnership Project (3GPP), 3GPP Long Term Evolution (LTE), and/or 3GPP LTE-Advanced (LTE-A) technologies and/or standards, including their predecessors, revisions, progeny, and/or variants. Additional examples of broadband wireless communication technologies/standards that may be utilized in some embodiments may include—without limitation—Global System for Mobile Communications (GSM)/Enhanced Data Rates for GSM Evolution (EDGE), Universal Mobile Telecommunications System (UMTS)/High Speed Packet Access (HSPA), and/or GSM with General Packet Radio Service (GPRS) system (GSM/GPRS), IEEE 802.16 wireless broadband standards such as IEEE 802.16m and/or IEEE 802.16p, International Mobile Telecommunications Advanced (IMT-ADV), Worldwide Interoperability for Microwave Access (WiMAX) and/or WiMAX II, Code Division Multiple Access (CDMA) 2000 (e.g., CDMA2000 1×RTT, CDMA2000 EV-DO, CDMA EV-DV, and so forth), High Performance Radio Metropolitan Area Network (HIPERMAN), Wireless Broadband (WiBro), High Speed Downlink Packet Access (HSDPA), High Speed Orthogonal Frequency-Division Multiplexing (OFDM) Packet Access (HSOPA), High-Speed Uplink Packet Access (HSUPA) technologies and/or standards, including their predecessors, revisions, progeny, and/or variants.

FIG. 1 illustrates an example of an operating environment 100 such as may be representative of various embodiments. In operating environment 100, a wearable wireless communication device (WCD) 102 is generally located within a wireless communication range 103 of a WCD 104. Wearable WCD 102 and WCD 104 may generally comprise electronic devices that are capable of wirelessly communicating with each other according to one or more wireless communication protocols. In some embodiments, wearable WCD 102 and WCD 104 may comprise Bluetooth Low Energy (BLE)-capable devices, and thus may be able to communicate with each other according to Bluetooth/BLE wireless communication techniques and/or protocols, such as—for example— Bluetooth Core Specification v. 4.2 and/or one or more predecessors, revisions, progeny, and/or variants. Examples of WCD 104 in various embodiments may include—without limitation—a desktop computer, a laptop computer, a tablet computer, a smartphone, a personal digital assistant (PDA), and an electronic reading device. In some embodiments, WCD 104 may comprise an electronic device mounted in a vehicle, such as a vehicle-mounted navigation system, stereo system, or entertainment system, for example. Wearable WCD 102 may generally comprise an electronic device that is designed/intended to be worn on/against some part of the human body. For example, in various embodiments, wearable WCD 102 may comprise a smart watch. In another example, in some embodiments, wearable WCD 102 may comprise smart glasses, or another type of optical head-mounted display. The embodiments are not limited to these examples.

In various embodiments, during ongoing operation, WCD 104 may generally be operative to provide one or more applications and/or services for user consumption. In some embodiments, with respect to some services and/or associated features of WCD 104, it may be desirable that WCD 104 exhibit different behaviors when the user is not nearby than it does when the user is nearby. For example, in various embodiments, when the user is away, it may be desirable that WCD 104 operate in a locked state in order to prevent unauthorized access and/or use of services and/or information available at WCD 104. In such embodiments, when the user is nearby, it may be desirable that WCD 104 operate in an unlocked state, so that the user is able to access and/or user such services and/or information. The embodiments are not limited to this example.

In some embodiments, it may be possible to configure WCD 104 to use the location of wearable WCD 102 as a proxy for the location of the user. More particularly, in various embodiments, it may be possible to configure WCD 104 to regard the user as being present when it detects that wearable WCD 102 is present, and to regard the user as being absent when it does not detect a presence of wearable WCD 102. For example, in some embodiments in which wearable WCD 102 and WCD 104 comprise BLE-capable devices, it may be possible to configure wearable WCD 102 to operate according to the Proximity Reporter role defined by the Proximity profile (PXP) v1.0.1 adopted by the Bluetooth Special Interest Group (SIG) Board of Directors (BoD) on Jul. 14, 2015 (hereinafter, "the BLE Proximity profile"), and to configure WCD 104 to operate according to the Proximity Monitor role defined by the BLE Proximity profile. The embodiments are not limited to this example.

In various embodiments, with respect to a given application, service, or feature, it may be possible to configure WCD 104 to behave differently depending on whether wearable WCD 102 is nearby. For example, in some embodiments, it may be possible to configure an auto-lock feature of WCD 104 to cause WCD 104 to operate in an unlocked state when wearable WCD 102 is nearby, and to otherwise cause WCD 104 to operate in a locked state. However, in various embodiments, the location of wearable WCD 102 may not necessarily constitute a reliable/accurate proxy for the location of the user. For example, if wearable WCD 102 comprises a smart watch that the user wears on some days but leaves on a desk near WCD 104 on other days, then WCD 104 may frequently conclude that the user is present when the user is actually absent. In some embodiments, such erroneous conclusions may have the potential to elicit undesirable behaviors on the part of WCD 104.

Disclosed herein are human proximity detection techniques that may be implemented in various embodiments in order enable more accurate and/or reliable user presence detection. According to some such techniques, a wearable WCD may be configured to use data obtained from one or more sensors to provide a remote WCD with an indication of whether the wearable WCD is actually being worn. In various embodiments, the data used may comprised heart rate data obtained from a heart rate sensor. In some embodiments, the heart rate data may be exposed by a Bluetooth Heart Rate Service (HRS) service. In various embodiments, the wearable WCD may expose its current transmit power to the remote WCD using a Bluetooth Transmit Power Service (TPS) service. In some embodiments, the remote WCD may determine an HPR state and/or an appropriate operating mode based on heart rate information received from the wearable WCD. The embodiments are not limited in this context.

Figure 2:
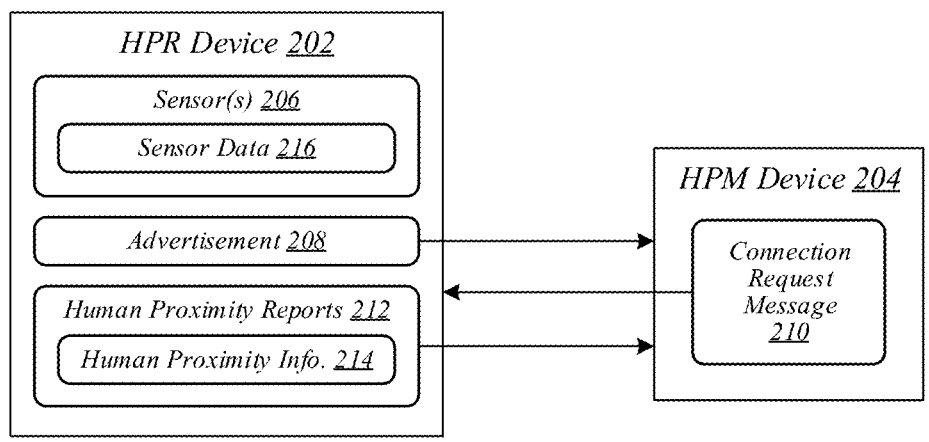
FIG. 2 illustrates an embodiment of a second operating environment.

FIG. 2 illustrates an example of an operating environment 200 that may be representative of the implementation of one or more of the disclosed human proximity detection techniques according to various embodiments. In operating environment 200, a human proximity reporting (HPR) device 202 may be implemented using a wearable WCD such as wearable WCD 102 of FIG. 1, and a human proximity monitoring (HPM) device 204 may be implemented using a WCD such as WCD 104 of FIG. 1. HPR device 202 may generally comprise a wearable WCD that is capable of reporting information indicating whether it is being worn. HPM device 204 may generally comprise a WCD that is configured, with respect to one or more applications, services, and/or associated features to behave in different ways depending on whether a user is nearby or not. In operating environment 200, HPM device 204 may be configured to perform determinations of whether a user is nearby based on information received from HPR device 202 via a wireless link.

In some embodiments, HPR device 202 and HPM device 204 may comprise BLE-capable devices, and the wireless link may comprise a BLE link. In various embodiments, HPR device 202 and HPM device 204 may operate in accordance with respective HPR and HPM roles that are defined in a BLE behavior profile. In some such embodiments, the BLE behavior profile may comprise an enhanced/modified version of a conventional BLE Proximity profile (PXP). In various embodiments, one or both of HPR device 202 and HPM device 204 may be configured to implement and/or utilize one or more Bluetooth/BLE services. In some embodiments, for example, one or both of HPR device 202 and HPM device 204 may be configured to implement and/or utilize a Bluetooth Link Loss Service (LLS) defining behavior to be exhibited in the event of a loss of a wireless link between two devices. In another example, in various embodiments, one or both of HPR device 202 and HPM device 204 may be configured to implement and/or utilize a Bluetooth Heart Rate Service (HRS) that exposes data including heart rate data from a heart rate sensor. In a third example, in some embodiments, one or both of HPR device 202 and HPM device 204 may be configured to implement and/or utilize a Bluetooth Tx Power Service (TPS) that exposes a current transmit power level for a device possessing a wireless connection to another device. The embodiments are not limited to these examples.

In various embodiments, HPR device 202 may be operative to transmit advertisement messages in order to notify nearby devices of its ability to serve as a human proximity reporter. In some embodiments, such advertisement messages may comprise BLE advertisement messages. In various embodiments, HPM device 204 may identify HPR device 202 based on a received advertisement 208 that comprises such an advertisement message. In some embodiments, based on advertising data comprised in advertisement 208, HPM device 204 may determine that HPR device 202 is capable of serving as a human proximity reporter. In various embodiments, in order to enable utilization of HPR device 202 as a human proximity reporter, HPM device 204 may initiate a connection establishment procedure to establish a wireless link with HPR device 202. In some embodiments, HPM device 204 may initiate the connection establishment procedure by sending a connection request message 210 to HPR device 202. In various embodiments in which the wireless link comprises a BLE link, connection request message 210 may comprise a BLE CONNECT_REQ protocol data unit (PDU). In some embodiments, connection request message 210 may comprise and/or indicate a request on the part of HPM device 204 to make use of human proximity reporting capabilities of HPR device 202. The embodiments are not limited in this context.

In various embodiments, following completion of an initial pairing process such as the aforementioned connection establishment procedure, HPR device 202 may begin transmitting human proximity reports 212 to HPM device 204. In some embodiments, HPR device 202 may transmit such human proximity reports 212 over the wireless link between HPR device 202 and HPM device 204. In various embodiments, HPM device 204 may monitor the wireless link for human proximity reports 212 of HPR device 202. In some embodiments, human proximity reports 212 may comprise human proximity information 214. Human proximity information 214 may generally comprise information indicating and/or usable to determine whether HPR device 202 is being worn by a user. In various embodiments, human proximity information 214 may comprise a direct indication of whether HPR device 202 is being worn by a user. For example, in some embodiments, HPR device 202 may provide a direct indication of whether HPR device 202 is being worn by a user by setting the value of a particular bit.

In various embodiments, human proximity information 214 may comprise an indirect indication of whether HPR device 202 is being worn by a user. The embodiments are not limited in this context.

In some embodiments, HPR device 202 may comprise one or more sensors 206. In various embodiments, sensor(s) 206 may include a heart rate sensor. In some embodiments, sensor(s) 206 may include a temperature sensor. In various embodiments, sensor(s) 206 may include one or more sensors for measuring electrical properties, such as resistance, impedance, capacitance, inductance, and so forth. In some embodiments, sensor(s) 206 may be operative to sense/measure one or more types of properties, characteristics, or conditions that may generally be indicative of whether HPR device 202 is being worn by a user. In various embodiments, for example, sensor(s) 206 may be configured to sense the presence (or absence) of a user heartbeat. The embodiments are not limited to this example.

In some embodiments, HPR device 202 may generate some or all of human proximity information 214 based on sensor data 216 provided by sensor(s) 206. Sensor data 216 may generally comprise data describing one or more types of properties, characteristics, or conditions measured by sensor(s) 206 that are indicative of whether HPR device 202 is being worn by a user. For example, in various embodiments, sensor data 216 may comprise a heart rate measurement provided by a heart rate sensor. In some embodiments, HPR device 202 may provide particular sensor data 216 itself as human proximity information 214, which may comprise an indirect indication of whether HPR device 202 is being worn by a user. For example, in various embodiments, sensor data 216 comprising a heart rate measurement may simply be passed along to HPM device 204 as human proximity information 214. In some embodiments, HPR device 202 may analyze sensor data 216 to determine whether it indicates that HPR device 202 is being worn by a user, and may then directly indicate its conclusion to HPM device 204 in the form of human proximity information 214. For example, in various embodiments, HPR device 202 may generate human proximity information 214 by setting a particular bit to either '0' or '1' depending on whether sensor data 216 comprising a heart rate measurement indicates a heart rate of zero or a heart rate that is greater than zero. The embodiments are not limited to these examples.

In some embodiments, during ongoing operation during which it makes use of the human proximity reporting capabilities of HPR device 202, HPM device 204 may be operative to track an applicable HPR state. In various embodiments, at a given point in time, the applicable HPR state may comprise one of a plurality of possible HPR states. In some embodiments, each such possible HPR state may correspond to a different respective set of circumstances/conditions. In various embodiments, the plurality of possible HPR states may include an HPR state that may be referred to as a Worn HPR Device (HPRD) state, an HPR state that may be referred to as an Unworn HPRD state, and an HPR state that may be referred to as an Unavailable/Distant (U/D) HPRD state. In some embodiments, the Worn HPRD state may correspond to circumstances in which HPR device 202 is worn by a user and is located in the vicinity of HPM device 204. In various embodiments, the Unworn HPRD state may correspond to circumstances in which HPR device 202 located in the vicinity of HPM device 204 but is not being worn by a user. In some embodiments, the U/D HPRD state may correspond to circumstances in which the wireless link between HPR device 202 and HPM device 204 has been lost, and/or in which HPR device 202 is not located in the vicinity of HPM device 204. It is to be appreciated that the names Worn HPRD state, Unworn HPRD state, and U/D HPRD state are purely exemplary, and the embodiments are not limited in this context.

In various embodiments, HPM device 204 may be operative to identify an applicable HPR state based on human proximity information 214 comprised in a given received human proximity report 212. In some embodiments, HPM device 204 may be operative to identify the applicable HPR state based on whether human proximity information 214 comprised in a given received human proximity report 212 indicates that HPR device 202 is being worn by a user. In various embodiments, HPM device 204 may be operative to determine an applicable HPR state based on information provided by one or more Bluetooth/BLE services. In some embodiments, for example, the human proximity information 214 based on which HPM device 204 identifies the applicable HPR state may comprise heart rate data exposed by a Bluetooth HRS service. In another example, in various embodiments, HPM device 204 may determine the applicable HPR state based on human proximity information 214 and on information provided by a Bluetooth LLS service. In some embodiments, HPM device 204 may consider information provided by a Bluetooth TPS service in conjunction with determining the applicable HPR state. For example, in various embodiments, a Bluetooth TPS service may be used to expose a value of a transmit power of HPR device 202, and HPM device 204 may consider that transmit power in conjunction with determining the applicable HPR state. The embodiments are not limited to these examples.

FIG. 3 illustrates an example of a state table 300 that may be representative of some embodiments in which HPM device 204 determines an applicable HPR state based on information provided by one or more of the aforementioned LLS, HRS, and TPS services. State table 300 illustrates respective combinations of LLS/TPS behaviors and HRS behaviors that may correspond to the Worn HPRD, Unworn HPRD, and U/D HPRD example HPR states discussed above. As shown in state table 300, the Worn HPRD state may be indicated when the HRS service exposes a heart rate value and the LLS service provides an alert that a Bluetooth connection between HPR device 202 and HPM device 204 is established or the TPS service exposes a higher transmit power level than a threshold value. The Unworn HPRD state may be indicated when the HRS service does not expose a heart rate value and the LLS service provides an alert that a Bluetooth connection between HPR device 202 and HPM device 204 is lost or the TPS service exposes a lower transmit power level than a threshold value. The U/D HPRD state may be indicated when the LLS service provides an alert that a Bluetooth connection between HPR device 202 and HPM device 204 is established or the TPS service exposes a higher transmit power level than a threshold value, but the HRS service does not expose a heart rate value. The embodiments are not limited to this example.

Returning to FIG. 2, in various embodiments, during ongoing operation, HPM device 204 may determine the behavior to be exhibited by a given application, service, or feature based on a determination of the HPR state. In some embodiments, following an initial pairing with HPR device 202, HPM device 204 may determine an initial HPR state, and may then determine an initial behavior/operating mode for a given application, service, or feature based on the initial HPR state. In various embodiments, HPM device 204 may determine the initial HPR state based on human proximity information 214 comprised in the first human proximity report 212 that it receives from HPR device 202 following the initial pairing. In some embodiments, HPM device 204 may identify the Worn HPRD state as the initial HPR state when human proximity information 214 comprised in the first human proximity report 212 indicates that HPR device 202 is being worn. In various embodiments, HPM device 204 may identify the Unworn HPRD state as the initial HPR state when human proximity information 214 comprised in the first human proximity report 212 indicates that HPR device 202 is not being worn. In some embodiments, HPM device 204 may subsequently track the HPR state to determine whether to change its behavior/operating mode with respect to the given application, service, or feature. In various embodiments, each time HPM device 204 receives new human proximity information 214 from HPR device 202, it may check the new human proximity information 214 to determine whether a change in HPR state is indicated. In some embodiments, HPM device 204 may be configured to reevaluate the HPR state in response to receipt of LLS service alerts and/or TPS service transmit power information. The embodiments are not limited in this context.

FIG. 4 illustrates an example of an operational mode table 400 that may be representative of an initial operating mode selection that HPM device 204 of FIG. 2 may perform based on the initial HPR state that it identifies following completion of initial pairing with HPR device 202 according to various embodiments. More particularly, operational mode table 400 may be representative of a selection of an initial operational mode for an auto-lock feature of HPM device 204, based on the initial HPR state. As shown in FIG. 4, if the initial HPR state is the Worn HPRD state, a human proximity trigger mode may be selected as the initial operating mode for the auto-lock feature. On the other hand, if the initial HPR state is the Unworn HPRD state, a timer trigger mode may be selected as the initial operating mode for the auto-lock feature. The embodiments are not limited to this example.

FIG. 5 illustrates an example of a state transition table 500 that may be representative of the implementation of one or more of the disclosed human proximity detection techniques according to some embodiments. For example, state transition table 500 may, according to various embodiments, be representative of HPR state transitions that may occur in operating environment 200 of FIG. 2 among the HPR states listed in state table 300 of FIG. 3. As shown in state transition table 500, a transition from the Unworn HPRD state to the Worn HPRD state may occur when the user puts on HPR device 202. A transition from the Worn HPRD state to the Unworn HPRD state may occur when the user takes off HPR device 202. A transition from the Worn HPRD state to the U/D HPRD state may occur when the user leaves the vicinity of HPM device 204 while wearing HPR device 202. A transition from the U/D HPRD state to the Worn HPRD state may occur when the user returns to the vicinity of HPM device 204 while wearing HPR device 202. The embodiments are not limited to these examples.

FIG. 6 illustrates an example of a behavior table 600 that may be representative of the implementation of one or more of the disclosed human proximity detection techniques according to some embodiments. Behavior table 600 may generally be representative of stipulated behaviors of an auto-lock feature of HPM device 204 in operating environment 200 of FIG. 2. More particularly, behavior table 600 may be representative of various behaviors to be exhibited by the auto-lock feature in response to various respective HPR state transitions. As shown in FIG. 6, in response to a transition from the Unworn HPRD state to the Worn HPRD state, the auto-lock feature may switch from timer trigger mode to human proximity trigger mode. In response to a transition from the Worn HPRD state to the Unworn HPRD state, the auto-lock feature may switch from human proximity trigger mode to timer trigger mode. In response to a transition from the Worn HPRD state to the U/D HPRD state, the auto-lock feature may lock HPM device 204. In response to a transition from the U/D HPRD state to the Worn HPRD state, the auto-lock feature may unlock HPM device 204. The embodiments are not limited to this example.

Operations for the above embodiments may be further described with reference to the following figures and accompanying examples. Some of the figures may include a logic flow. Although such figures presented herein may include a particular logic flow, it can be appreciated that the logic flow merely provides an example of how the general functionality as described herein can be implemented. Further, the given logic flow does not necessarily have to be executed in the order presented unless otherwise indicated. In addition, the given logic flow may be implemented by a hardware element, a software element executed by a processor, or any combination thereof. The embodiments are not limited in this context.

Figure 7:
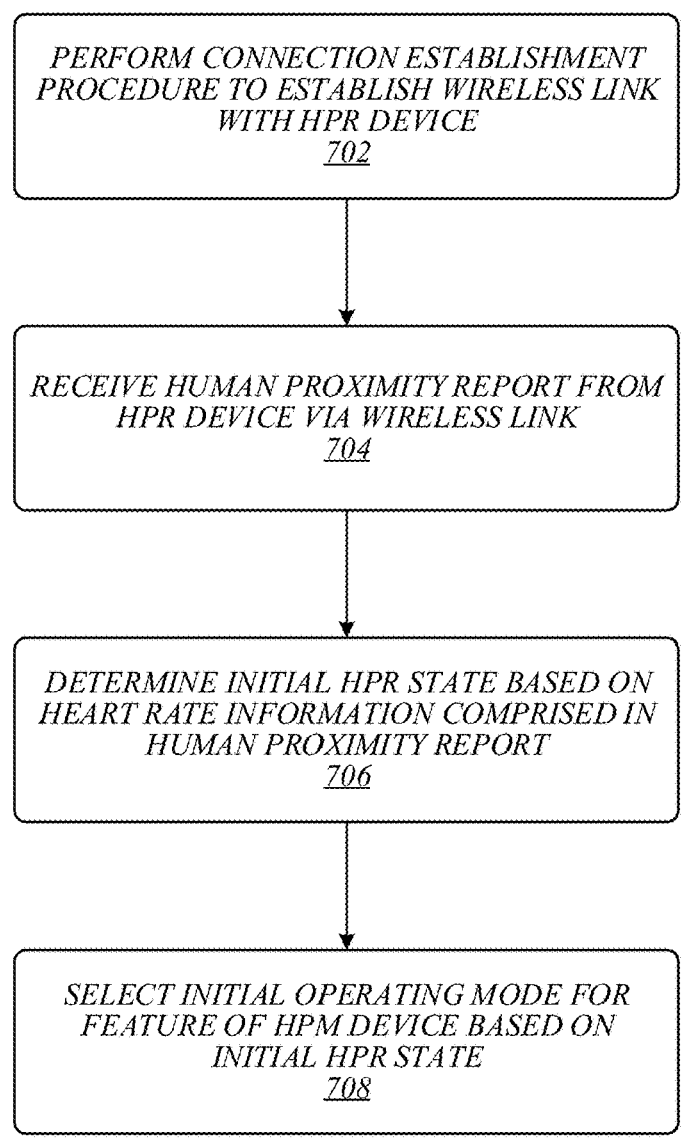
FIG. 7 illustrates an embodiment of a first logic flow.

FIG. 7 illustrates an example of a logic flow 700 that may be representative of one or more of the disclosed human proximity detection techniques according to various embodiments. For example, logic flow 700 may be representative of operations that may be performed by HPM device 204 in operating environment 200 of FIG. 2 according to some embodiments. As shown in FIG. 7, a connection establishment procedure may be performed at 702 to establish a wireless link with an HPR device. For example, in operating environment 200 of FIG. 2, HPM device 204 may be operative to perform a connection establishment procedure to establish a wireless link with HPR device 202. At 704, a human proximity report may be received from the HPR device via the wireless link. For example, in operating environment 200 of FIG. 2, HPM device 204 may be operative to receive a human proximity report 212 from HPR device 202 via a wireless link established at 702.

At 706, an initial HPR state may be determined based on heart rate information comprised in the received human proximity report. For example, in operating environment 200 of FIG. 2, a human proximity report 212 that HPM device 204 receives from HPR device 202 may contain human proximity information 214 that comprises heart rate information, and HPM device 204 may be operative to determine an initial HPR state based on that heart rate information. At 708, an initial operating mode may be selected for a feature of the HPM device based on the initial HPR state. For example, in operating environment 200 of FIG. 2, HPM device 204 may be operative to select an initial operating mode for an auto-lock feature based on an initial HPR state determined at 706. The embodiments are not limited to these examples.

Figure 8:
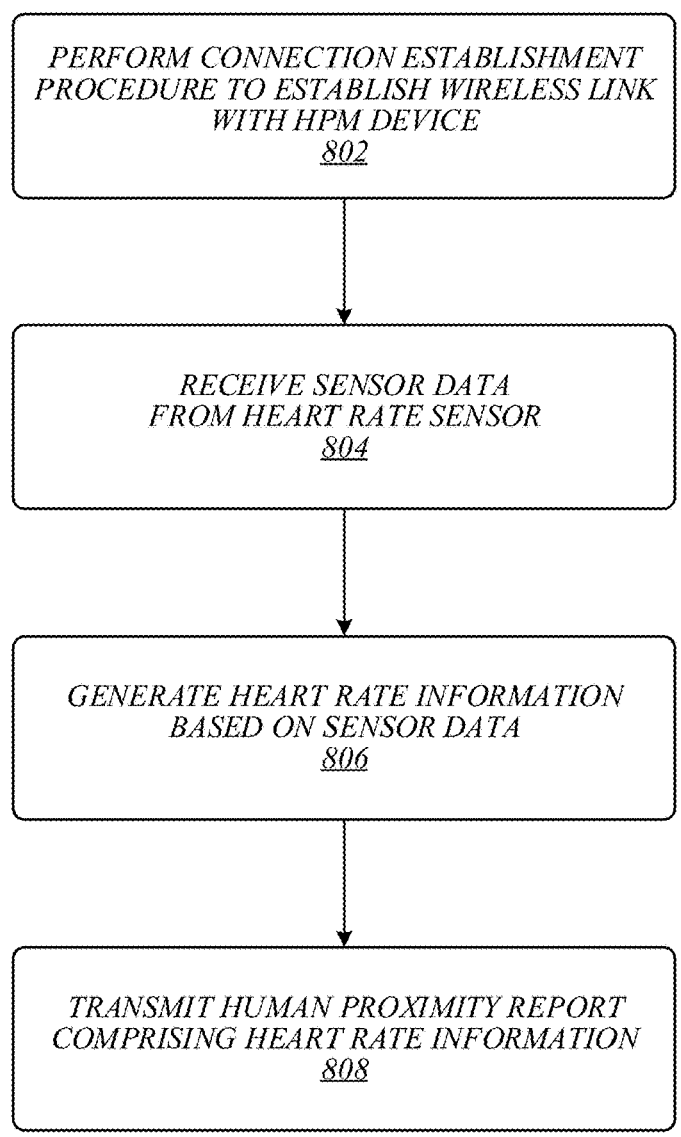
FIG. 8 illustrates an embodiment of a second logic flow.

FIG. 8 illustrates an example of a logic flow 800 that may be representative of one or more of the disclosed human proximity detection techniques according to various embodiments. For example, logic flow 800 may be representative of operations that may be performed by HPR device 202 in operating environment 200 of FIG. 2 according to some embodiments. As shown in FIG. 8, a connection establishment procedure may be performed at 802 to establish a wireless link with an HPM device. For example, in operating environment 200 of FIG. 2, HPR device 202 may be operative to perform a connection establishment procedure to establish a wireless link with HPM device 202.

At 804, sensor data may be received from a heart rate sensor. For example, in operating environment 200 of FIG. 2, HPR device 202 may be operative to receive sensor data 216 from a sensor 206 that comprises a heart rate sensor. At 806, heart rate information may be generated based on the received sensor data. For example, in operating environment 200 of FIG. 2, HPR device 202 may be operative to generate heart rate information based on sensor data received at 804. At 808, a human proximity report may be transmitted that comprises the heart rate information. For example, in operating environment 200 of FIG. 2, HPR device 202 may be operative to include heart rate information generated at 806 as human proximity information 214 in a human proximity report 212 that it transmits to HPM device 204. The embodiments are not limited to these examples.

Various embodiments of the invention may be implemented fully or partially in software and/or firmware. This software and/or firmware may take the form of instructions contained in or on a non-transitory computer-readable storage medium. Those instructions may then be read and executed by one or more processors to enable performance of the operations described herein. The instructions may be in any suitable form, such as but not limited to source code, compiled code, interpreted code, executable code, static code, dynamic code, and the like. Such a computer-readable medium may include any tangible non-transitory medium for storing information in a form readable by one or more computers, such as but not limited to read only memory (ROM); random access memory (RAM); magnetic disk storage media; optical storage media; a flash memory, etc. The embodiments are not limited in this context.

Figure 9:
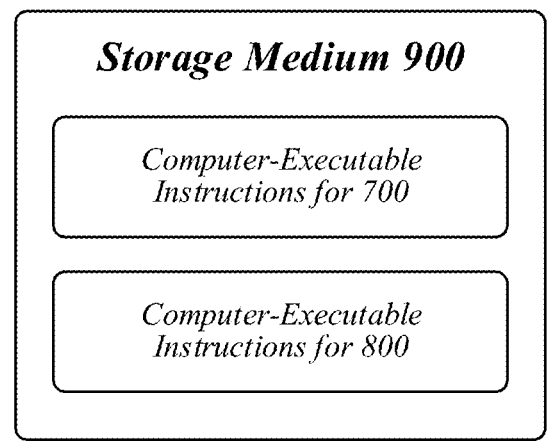
FIG. 9 illustrates an embodiment of a storage medium.

FIG. 9 illustrates an embodiment of a storage medium 900. Storage medium 900 may comprise any non-transitory computer-readable storage medium or machine-readable storage medium, such as an optical, magnetic or semiconductor storage medium. In various embodiments, storage medium 900 may comprise an article of manufacture. In some embodiments, storage medium 900 may store computer-executable instructions, such as computer-executable instructions to implement one or both of logic flow 700 of FIG. 7 and logic flow 800 of FIG. 8. Examples of a computer-readable storage medium or machine-readable storage medium may include any tangible media capable of storing electronic data, including volatile memory or non-volatile memory, removable or non-removable memory, erasable or non-erasable memory, writeable or re-writeable memory, and so forth. Examples of computer-executable instructions may include any suitable type of code, such as source code, compiled code, interpreted code, executable code, static code, dynamic code, object-oriented code, visual code, and the like. The embodiments are not limited in this context.

Figure 10:
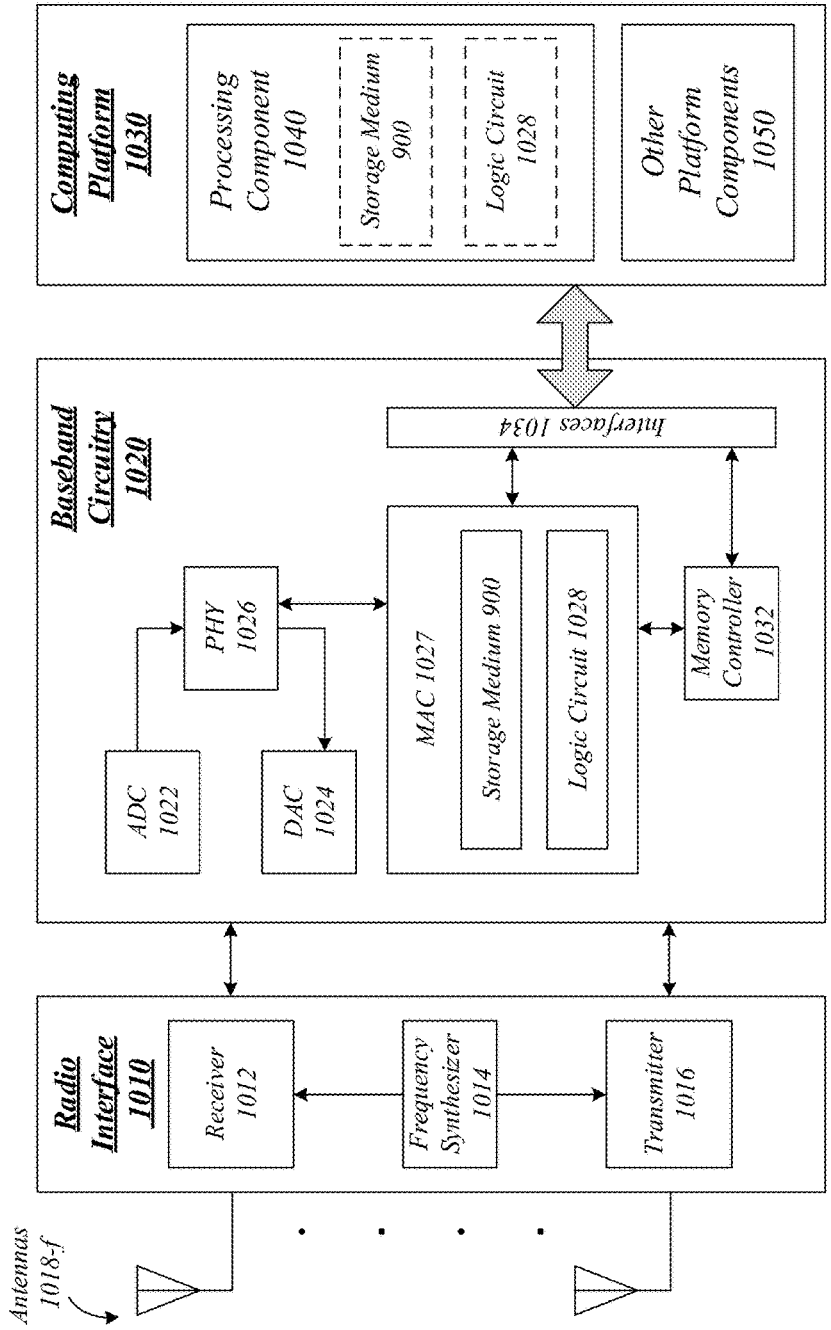
FIG. 10 illustrates an embodiment of a device.

FIG. 10 illustrates an embodiment of a communications device 1000 that may implement one or more of HPR device 202 and HPM device 204 of FIG. 2, logic flow 700 of FIG. 7, logic flow 800 of FIG. 8, and storage medium 900 of FIG. 9. In various embodiments, device 1000 may comprise a logic circuit 1028. The logic circuit 1028 may include physical circuits to perform operations described for one or more of HPR device 202 and HPM device 204 of FIG. 2, logic flow 700 of FIG. 7, and logic flow 800 of FIG. 8, for example. As shown in FIG. 10, device 1000 may include a radio interface 1010, baseband circuitry 1020, and computing platform 1030, although the embodiments are not limited to this configuration.

The device 1000 may implement some or all of the structure and/or operations for one or more of HPR device 202 and HPM device 204 of FIG. 2, logic flow 700 of FIG. 7, logic flow 800 of FIG. 8, storage medium 900 of FIG. 9, and logic circuit 1028 in a single computing entity, such as entirely within a single device. Alternatively, the device 1000 may distribute portions of the structure and/or operations for one or more of HPR device 202 and HPM device 204 of FIG. 2, logic flow 700 of FIG. 7, logic flow 800 of FIG. 8, storage medium 900 of FIG. 9, and logic circuit 1028 across multiple computing entities using a distributed system architecture, such as a client-server architecture, a 3-tier architecture, an N-tier architecture, a tightly-coupled or clustered architecture, a peer-to-peer architecture, a master-slave architecture, a shared database architecture, and other types of distributed systems. The embodiments are not limited in this context.

In one embodiment, radio interface 1010 may include a component or combination of components adapted for transmitting and/or receiving single-carrier or multi-carrier modulated signals (e.g., including complementary code keying (CCK), orthogonal frequency division multiplexing (OFDM), and/or single-carrier frequency division multiple access (SC-FDMA) symbols) although the embodiments are not limited to any specific over-the-air interface or modulation scheme. Radio interface 1010 may include, for example, a receiver 1012, a frequency synthesizer 1014, and/or a transmitter 1016. Radio interface 1010 may include bias controls, a crystal oscillator and/or one or more antennas 1018-*f*. In another embodiment, radio interface 1010 may use external voltage-controlled oscillators (VCOs), surface acoustic wave filters, intermediate frequency (IF) filters and/or RF filters, as desired. Due to the variety of potential RF interface designs an expansive description thereof is omitted.

Baseband circuitry 1020 may communicate with radio interface 1010 to process receive and/or transmit signals and may include, for example, an analog-to-digital converter 1022 for down converting received signals, a digital-to-analog converter 1024 for up converting signals for transmission. Further, baseband circuitry 1020 may include a baseband or physical layer (PHY) processing circuit 1026 for PHY link layer processing of respective receive/transmit signals. Baseband circuitry 1020 may include, for example, a medium access control (MAC) processing circuit 1027 for MAC/data link layer processing. Baseband circuitry 1020 may include a memory controller 1032 for communicating with MAC processing circuit 1027 and/or a computing platform 1030, for example, via one or more interfaces 1034.

In some embodiments, PHY processing circuit 1026 may include a frame construction and/or detection module, in combination with additional circuitry such as a buffer memory, to construct and/or deconstruct communication frames. Alternatively or in addition, MAC processing circuit 1027 may share processing for certain of these functions or perform these processes independent of PHY processing circuit 1026. In some embodiments, MAC and PHY processing may be integrated into a single circuit.

The computing platform 1030 may provide computing functionality for the device 1000. As shown, the computing platform 1030 may include a processing component 1040. In addition to, or alternatively of, the baseband circuitry 1020, the device 1000 may execute processing operations or logic for one or more of HPR device 202 and HPM device 204 of FIG. 2, logic flow 700 of FIG. 7, logic flow 800 of FIG. 8, storage medium 900 of FIG. 9, and logic circuit 1028 using the processing component 1040. The processing component 1040 (and/or PHY 1026 and/or MAC 1027) may comprise various hardware elements, software elements, or a combination of both. Examples of hardware elements may include devices, logic devices, components, processors, microprocessors, circuits, processor circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints, as desired for a given implementation.

The computing platform 1030 may further include other platform components 1050. Other platform components 1050 include common computing elements, such as one or more processors, multi-core processors, co-processors, memory units, chipsets, controllers, peripherals, interfaces, oscillators, timing devices, video cards, audio cards, multimedia input/output (I/O) components (e.g., digital displays), power supplies, and so forth. Examples of memory units may include without limitation various types of computer readable and machine readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information.

Device 1000 may be, for example, an ultra-mobile device, a mobile device, a fixed device, a machine-to-machine (M2M) device, a personal digital assistant (PDA), a mobile computing device, a smart phone, a telephone, a digital telephone, a cellular telephone, user equipment, eBook readers, a handset, a one-way pager, a two-way pager, a messaging device, a computer, a personal computer (PC), a desktop computer, a laptop computer, a notebook computer, a netbook computer, a handheld computer, a tablet computer, a server, a server array or server farm, a web server, a network server, an Internet server, a work station, a minicomputer, a main frame computer, a supercomputer, a network appliance, a web appliance, a distributed computing system, multiprocessor systems, processor-based systems, consumer electronics, programmable consumer electronics, game devices, display, television, digital television, set top box, wireless access point, base station, node B, subscriber station, mobile subscriber center, radio network controller, router, hub, gateway, bridge, switch, machine, or combination thereof. Accordingly, functions and/or specific configurations of device 1000 described herein, may be included or omitted in various embodiments of device 1000, as suitably desired.

Embodiments of device 1000 may be implemented using single input single output (SISO) architectures. However, certain implementations may include multiple antennas (e.g., antennas 1018-*f*) for transmission and/or reception using adaptive antenna techniques for beamforming or spatial division multiple access (SDMA) and/or using MIMO communication techniques.

The components and features of device 1000 may be implemented using any combination of discrete circuitry, application specific integrated circuits (ASICs), logic gates and/or single chip architectures. Further, the features of device 1000 may be implemented using microcontrollers, programmable logic arrays and/or microprocessors or any combination of the foregoing where suitably appropriate. It is noted that hardware, firmware and/or software elements may be collectively or individually referred to herein as "logic" or "circuit."

It should be appreciated that the exemplary device 1000 shown in the block diagram of FIG. 10 may represent one functionally descriptive example of many potential implementations. Accordingly, division, omission or inclusion of block functions depicted in the accompanying figures does not infer that the hardware components, circuits, software and/or elements for implementing these functions would be necessarily be divided, omitted, or included in embodiments.

Figure 11:
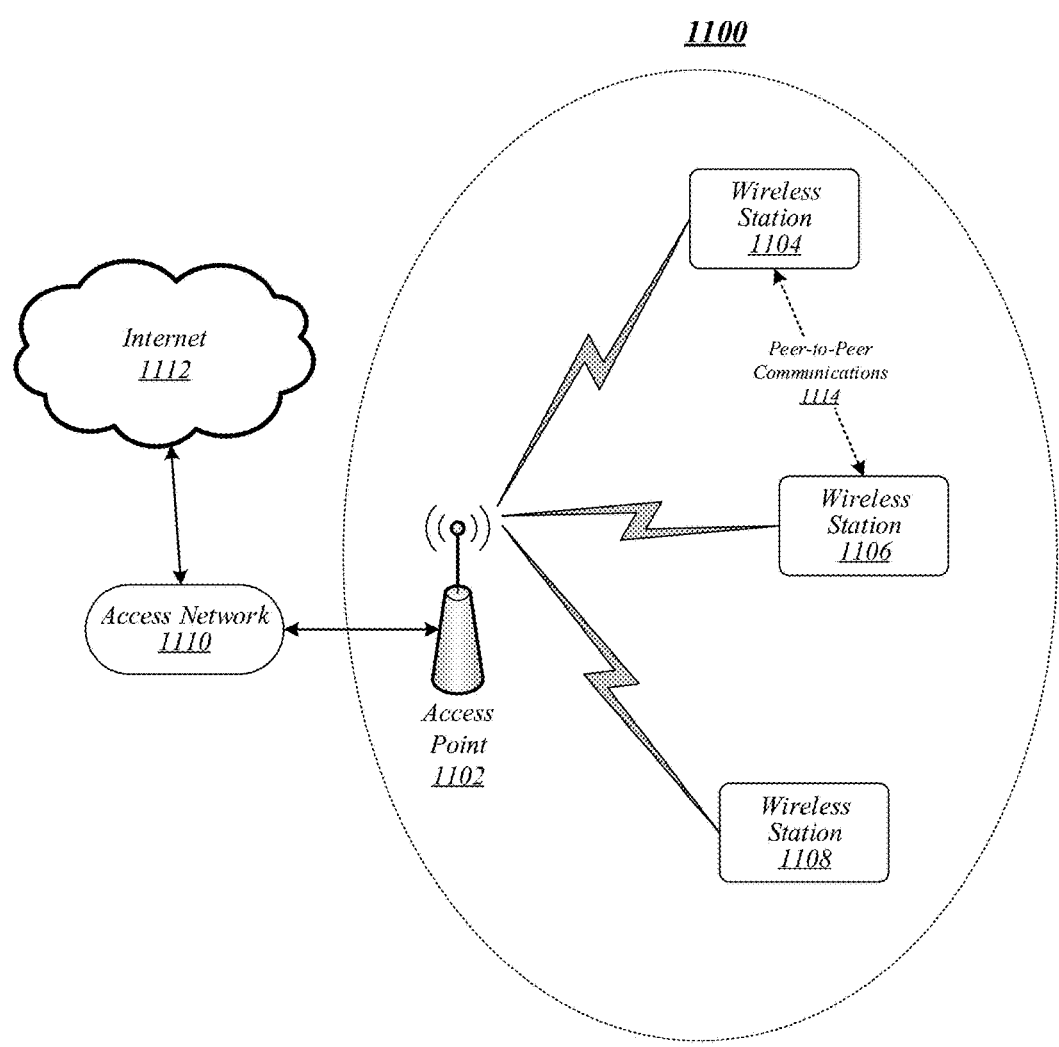
FIG. 11 illustrates an embodiment of a wireless network.

FIG. 11 illustrates an embodiment of a wireless network 1100. As shown in FIG. 11, wireless network comprises an access point 1102 and wireless stations 1104, 1106, and 1108. In various embodiments, wireless network 1100 may comprise a wireless local area network (WLAN), such as a WLAN implementing one or more Institute of Electrical and Electronics Engineers (IEEE) 802.11 standards (sometimes collectively referred to as "Wi-Fi"). In some other embodiments, wireless network 1100 may comprise another type of wireless network, and/or may implement other wireless communications standards. In various embodiments, for example, wireless network 1100 may comprise a WWAN or WPAN rather than a WLAN. The embodiments are not limited to this example.

In some embodiments, wireless network 1100 may implement one or more broadband wireless communications standards, such as 3G or 4G standards, including their revisions, progeny, and variants. Examples of 3G or 4G wireless standards may include without limitation any of the IEEE 802.16m and 802.16p standards, 3rd Generation Partnership Project (3GPP) Long Term Evolution (LTE) and LTE-Advanced (LTE-A) standards, and International Mobile Telecommunications Advanced (IMT-ADV) standards, including their revisions, progeny and variants. Other suitable examples may include, without limitation, Global System for Mobile Communications (GSM)/Enhanced Data Rates for GSM Evolution (EDGE) technologies, Universal Mobile Telecommunications System (UMTS)/High Speed Packet Access (HSPA) technologies, Worldwide Interoperability for Microwave Access (WiMAX) or the WiMAX II technologies, Code Division Multiple Access (CDMA) 2000 system technologies (e.g., CDMA2000 1xRTT, CDMA2000 EV-DO, CDMA EV-DV, and so forth), High Performance Radio Metropolitan Area Network (HIPERMAN) technologies as defined by the European Telecommunications Standards Institute (ETSI) Broadband Radio Access Networks (BRAN), Wireless Broadband (WiBro) technologies, GSM with General Packet Radio Service (GPRS) system (GSM/GPRS) technologies, High Speed Downlink Packet Access (HSDPA) technologies, High Speed Orthogonal Frequency-Division Multiplexing (OFDM) Packet Access (HSOPA) technologies, High-Speed Uplink Packet Access (HSUPA) system technologies, 3GPP Rel. 8-12 of LTE/System Architecture Evolution (SAE), and so forth. The embodiments are not limited in this context.

In various embodiments, wireless stations 1104, 1106, and 1108 may communicate with access point 1102 in order to obtain connectivity to one or more external data networks. In some embodiments, for example, wireless stations 1104, 1106, and 1108 may connect to the Internet 1112 via access point 1102 and access network 1110. In various embodiments, access network 1110 may comprise a private network that provides subscription-based Internet-connectivity, such as an Internet Service Provider (ISP) network. The embodiments are not limited to this example.

In various embodiments, two or more of wireless stations 1104, 1106, and 1108 may communicate with each other directly by exchanging peer-to-peer communications. For example, in the example of FIG. 11, wireless stations 1104 and 1106 communicate with each other directly by exchanging peer-to-peer communications 1114. In some embodiments, such peer-to-peer communications may be performed according to one or more Wi-Fi Alliance (WFA) standards. For example, in various embodiments, such peer-to-peer communications may be performed according to the WFA Wi-Fi Direct standard, 2010 Release. In various embodiments, such peer-to-peer communications may additionally or alternatively be performed using one or more interfaces, protocols, and/or standards developed by the WFA Wi-Fi Direct Services (WFDS) Task Group. The embodiments are not limited to these examples.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that actually make the logic or processor. Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

The following examples pertain to further embodiments:

Example 1 is an apparatus, comprising a memory, and logic, at least a portion of the logic comprised in circuitry coupled to the memory, the logic to perform a connection establishment procedure to establish a wireless link with a human proximity reporting (HPR) device, identify heart rate information comprised in a human proximity report received from the HPR device via the wireless link, determine an initial HPR state based on the heart rate information, and select an initial operating mode for a feature of a human proximity monitoring (HPM) device based on the initial HPR state.

Example 2 is the apparatus of Example 1, the logic to determine the initial HPR state based on whether the heart rate information indicates a detection of a human heart rate.

Example 3 is the apparatus of any of Examples 1 to 2, the heart rate information to comprise information exposed by a heart rate service (HRS).

Example 4 is the apparatus of any of Examples 1 to 3, the feature to comprise an auto-lock feature.

Example 5 is the apparatus of Example 4, the initial operating mode to comprise a timer trigger mode or a human proximity trigger mode.

Example 6 is the apparatus of any of Examples 1 to 5, the logic to transition the HPM device from the initial operating mode to a second operating mode in response to an alert indicating a loss of the wireless link.

Example 7 is the apparatus of Example 6, the alert to comprise an alert of a Bluetooth Link Loss Service (LLS) service.

Example 8 is the apparatus of any of Examples 1 to 7, the logic to transition the HPM device from the initial operating mode to a second operating mode in response to a determination that a transmit power of the HPR device is lower than a threshold value.

Example 9 is the apparatus of Example 8, the transmit power of the HPR device to be exposed by a Bluetooth Transmit Power Service (TPS) service.

Example 10 is the apparatus of any of Examples 1 to 9, the logic to identify the HPR device based on a received advertisement message.

Example 11 is the apparatus of any of Examples 1 to 10, the logic to include logic for operating according to an HPM device role defined by a Bluetooth Low Energy (BLE) behavior profile.

Example 12 is the apparatus of Example 11, the BLE behavior profile to comprise a Proximity profile (PXP).

Example 13 is a system, comprising an apparatus according to any of Examples 1 to 12, and at least one radio frequency (RF) transceiver.

Example 14 is the system of Example 13, comprising at least one processor.

Example 15 is the system of any of Examples 13 to 14, comprising at least one RF antenna.

Example 16 is a wireless communication device, comprising a system according to any of Examples 13 to 15, and a display.

Example 17 is an apparatus, comprising a memory, and logic for a human proximity reporting (HPR) device, at least a portion of the logic comprised in circuitry coupled to the memory, the logic to perform a connection establishment procedure to establish a wireless link with a human proximity monitoring (HPM) device, generate heart rate information based on sensor data received from a heart rate sensor, and generate a human proximity report for transmission to the HPM device via the wireless link, the human proximity report to comprise the heart rate information.

Example 18 is the apparatus of Example 17, the sensor data to be exposed by a Bluetooth Heart Rate Service (HRS) service.

Example 19 is the apparatus of any of Examples 17 to 18, the logic to expose a current transmit power of the HPR device to the HPM device.

Example 20 is the apparatus of Example 19, the current transmit power of the HPR device to be exposed to the HPM device using a Bluetooth Transmit Power Service (TPS) service.

Example 21 is the apparatus of any of Examples 17 to 20, the logic to include logic for operating according to an HPR device role defined by a Bluetooth Low Energy (BLE) behavior profile.

Example 22 is the apparatus of Example 21, the BLE behavior profile to comprise a Proximity profile (PXP).

Example 23 is the apparatus of any of Examples 17 to 22, the logic to monitor a status of the wireless link with the HPM device.

Example 24 is the apparatus of Example 23, the logic to monitor the status of the wireless link using a Bluetooth Link Loss Service (LLS) service.

Example 25 is the apparatus of any of Examples 17 to 24, the logic to generate an advertisement message for transmission over a Bluetooth Low Energy (BLE) advertising channel.

Example 26 is the apparatus of Example 25, the advertisement message to comprise an identifier associated with the HPR device.

Example 27 is the apparatus of any of Examples 25 to 26, the advertisement message to comprise an indication of an availability of a human proximity reporting service.

Example 28 is a system, comprising an apparatus according to any of Examples 17 to 27, and at least one radio frequency (RF) transceiver.

Example 29 is the system of Example 28, comprising at least one processor.

Example 30 is the system of any of Examples 28 to 29, comprising at least one RF antenna.

Example 31 is a wearable wireless communication device, comprising a system according to any of Examples 28 to 30, and a display.

Example 32 is the wearable wireless communication device of Example 31, the display comprising a touchscreen display.

Example 33 is at least one non-transitory computer-readable storage medium comprising a set of instructions that, in response to being executed on a computing device, cause the computing device to perform a connection establishment procedure to establish a wireless link with a human proximity reporting (HPR) device, identify heart rate information comprised in a human proximity report received from the HPR device via the wireless link, determine an initial HPR state based on the heart rate information, and select an initial operating mode for a feature of a human proximity monitoring (HPM) device based on the initial HPR state.

Example 34 is the at least one non-transitory computer-readable storage medium of Example 33, comprising instructions that, in response to being executed on the computing device, cause the computing device to determine the initial HPR state based on whether the heart rate information indicates a detection of a human heart rate.

Example 35 is the at least one non-transitory computer-readable storage medium of any of Examples 33 to 34, the heart rate information to comprise information exposed by a heart rate service (HRS).

Example 36 is the at least one non-transitory computer-readable storage medium of any of Examples 33 to 35, the feature to comprise an auto-lock feature.

Example 37 is the at least one non-transitory computer-readable storage medium of Example 36, the initial operating mode to comprise a timer trigger mode or a human proximity trigger mode.

Example 38 is the at least one non-transitory computer-readable storage medium of any of Examples 33 to 37, comprising instructions that, in response to being executed on the computing device, cause the computing device to transition the HPM device from the initial operating mode to a second operating mode in response to an alert indicating a loss of the wireless link.

Example 39 is the at least one non-transitory computer-readable storage medium of Example 38, the alert to comprise an alert of a Bluetooth Link Loss Service (LLS) service.

Example 40 is the at least one non-transitory computer-readable storage medium of any of Examples 33 to 39, comprising instructions that, in response to being executed on the computing device, cause the computing device to transition the HPM device from the initial operating mode to a second operating mode in response to a determination that a transmit power of the HPR device is lower than a threshold value.

Example 41 is the at least one non-transitory computer-readable storage medium of Example 40, the transmit power of the HPR device to be exposed by a Bluetooth Transmit Power Service (TPS) service.

Example 42 is the at least one non-transitory computer-readable storage medium of any of Examples 33 to 41, comprising instructions that, in response to being executed on the computing device, cause the computing device to identify the HPR device based on a received advertisement message.

Example 43 is the at least one non-transitory computer-readable storage medium of any of Examples 33 to 42, comprising instructions that, in response to being executed on the computing device, cause the computing device to operate according to an HPM device role defined by a Bluetooth Low Energy (BLE) behavior profile.

Example 44 is the at least one non-transitory computer-readable storage medium of Example 43, the BLE behavior profile to comprise a Proximity profile (PXP).

Example 45 is at least one non-transitory computer-readable storage medium comprising a set of instructions that, in response to being executed on a computing device, cause the computing device to perform a connection establishment procedure to establish a wireless link with a human proximity monitoring (HPM) device, generate heart rate information based on sensor data received from a heart rate sensor, and generate a human proximity report for transmission to the HPM device via the wireless link, the human proximity report to comprise the heart rate information.

Example 46 is the at least one non-transitory computer-readable storage medium of Example 45, the sensor data to be exposed by a Bluetooth Heart Rate Service (HRS) service.

Example 47 is the at least one non-transitory computer-readable storage medium of any of Examples 45 to 46, comprising instructions that, in response to being executed on the computing device, cause the computing device to expose a current transmit power of the HPR device to the HPM device.

Example 48 is the at least one non-transitory computer-readable storage medium of Example 47, the current transmit power of the HPR device to be exposed to the HPM device using a Bluetooth Transmit Power Service (TPS) service.

Example 49 is the at least one non-transitory computer-readable storage medium of any of Examples 45 to 48, comprising instructions that, in response to being executed on the computing device, cause the computing device to operate according to an HPR device role defined by a Bluetooth Low Energy (BLE) behavior profile.

Example 50 is the at least one non-transitory computer-readable storage medium of Example 49, the BLE behavior profile to comprise a Proximity profile (PXP).

Example 51 is the at least one non-transitory computer-readable storage medium of any of Examples 45 to 50, comprising instructions that, in response to being executed on the computing device, cause the computing device to monitor a status of the wireless link with the HPM device.

Example 52 is the at least one non-transitory computer-readable storage medium of Example 51, comprising instructions that, in response to being executed on the computing device, cause the computing device to monitor the status of the wireless link using a Bluetooth Link Loss Service (LLS) service.

Example 53 is the at least one non-transitory computer-readable storage medium of any of Examples 45 to 52, comprising instructions that, in response to being executed on the computing device, cause the computing device to generate an advertisement message for transmission over a Bluetooth Low Energy (BLE) advertising channel.

Example 54 is the at least one non-transitory computer-readable storage medium of Example 53, the advertisement message to comprise an identifier associated with the HPR device.

Example 55 is the at least one non-transitory computer-readable storage medium of any of Examples 53 to 54, the advertisement message to comprise an indication of an availability of a human proximity reporting service.

Example 56 is a method, comprising performing a connection establishment procedure to establish a wireless link with a human proximity reporting (HPR) device, identifying heart rate information comprised in a human proximity report received from the HPR device via the wireless link, determining an initial HPR state based on the heart rate information, and selecting an initial operating mode for a feature of a human proximity monitoring (HPM) device based on the initial HPR state.

Example 57 is the method of Example 56, comprising determining the initial HPR state based on whether the heart rate information indicates a detection of a human heart rate.

Example 58 is the method of any of Examples 56 to 57, the heart rate information to comprise information exposed by a heart rate service (HRS).

Example 59 is the method of any of Examples 56 to 58, the feature to comprise an auto-lock feature.

Example 60 is the method of Example 59, the initial operating mode to comprise a timer trigger mode or a human proximity trigger mode.

Example 61 is the method of any of Examples 56 to 60, comprising transitioning the HPM device from the initial operating mode to a second operating mode in response to an alert indicating a loss of the wireless link.

Example 62 is the method of Example 61, the alert to comprise an alert of a Bluetooth Link Loss Service (LLS) service.

Example 63 is the method of any of Examples 56 to 62, comprising transitioning the HPM device from the initial operating mode to a second operating mode in response to a determination that a transmit power of the HPR device is lower than a threshold value.

Example 64 is the method of Example 63, the transmit power of the HPR device to be exposed by a Bluetooth Transmit Power Service (TPS) service.

Example 65 is the method of any of Examples 56 to 64, comprising identifying the HPR device based on a received advertisement message.

Example 66 is the method of any of Examples 56 to 65, comprising operating according to an HPM device role defined by a Bluetooth Low Energy (BLE) behavior profile.

Example 67 is the method of Example 66, the BLE behavior profile to comprise a Proximity profile (PXP).

Example 68 is at least one non-transitory computer-readable storage medium comprising a set of instructions that, in response to being executed on a computing device, cause the computing device to perform a method according to any of Examples 56 to 67.

Example 69 is an apparatus, comprising means for performing a method according to any of Examples 56 to 67.

Example 70 is a system, comprising the apparatus of Example 69, and at least one radio frequency (RF) transceiver.

Example 71 is the system of Example 70, comprising at least one processor.

Example 72 is the system of any of Examples 70 to 71, comprising at least one RF antenna.

Example 73 is a wireless communication device, comprising a system according to any of Examples 70 to 72, and a display.

Example 74 is a method, comprising performing a connection establishment procedure to establish a wireless link with a human proximity monitoring (HPM) device, generating heart rate information based on sensor data received from a heart rate sensor, and generating a human proximity report for transmission to the HPM device via the wireless link, the human proximity report to comprise the heart rate information.

Example 75 is the method of Example 74, the sensor data to be exposed by a Bluetooth Heart Rate Service (HRS) service.

Example 76 is the method of any of Examples 74 to 75, comprising exposing a current transmit power of the HPR device to the HPM device.

Example 77 is the method of Example 76, the current transmit power of the HPR device to be exposed to the HPM device using a Bluetooth Transmit Power Service (TPS) service.

Example 78 is the method of any of Examples 74 to 77, comprising operating according to an HPR device role defined by a Bluetooth Low Energy (BLE) behavior profile.

Example 79 is the method of Example 78, the BLE behavior profile to comprise a Proximity profile (PXP).

Example 80 is the method of any of Examples 74 to 79, comprising monitoring a status of the wireless link with the HPM device.

Example 81 is the method of Example 80, comprising monitoring the status of the wireless link using a Bluetooth Link Loss Service (LLS) service.

Example 82 is the method of any of Examples 74 to 81, comprising generating an advertisement message for transmission over a Bluetooth Low Energy (BLE) advertising channel.

Example 83 is the method of Example 82, the advertisement message to comprise an identifier associated with the HPR device.

Example 84 is the method of any of Examples 82 to 83, the advertisement message to comprise an indication of an availability of a human proximity reporting service.

Example 85 is at least one non-transitory computer-readable storage medium comprising a set of instructions that, in response to being executed on a computing device, cause the computing device to perform a method according to any of Examples 74 to 84.

Example 86 is an apparatus, comprising means for performing a method according to any of Examples 74 to 84.

Example 87 is a system, comprising the apparatus of Example 86, and at least one radio frequency (RF) transceiver.

Example 88 is the system of Example 87, comprising at least one processor.

Example 89 is the system of any of Examples 87 to 88, comprising at least one RF antenna.

Example 90 is a wearable wireless communication device, comprising a system according to any of Examples 87 to 89, and a display.

Example 91 is the wearable wireless communication device of Example 90, the display comprising a touchscreen display.

Example 92 is an apparatus, comprising means for performing a connection establishment procedure to establish a wireless link with a human proximity reporting (HPR) device, means for identifying heart rate information comprised in a human proximity report received from the HPR device via the wireless link, means for determining an initial HPR state based on the heart rate information, and means for selecting an initial operating mode for a feature of a human proximity monitoring (HPM) device based on the initial HPR state.

Example 93 is the apparatus of Example 92, comprising means for determining the initial HPR state based on whether the heart rate information indicates a detection of a human heart rate.

Example 94 is the apparatus of any of Examples 92 to 93, the heart rate information to comprise information exposed by a heart rate service (HRS).

Example 95 is the apparatus of any of Examples 92 to 94, the feature to comprise an auto-lock feature.

Example 96 is the apparatus of Example 95, the initial operating mode to comprise a timer trigger mode or a human proximity trigger mode.

Example 97 is the apparatus of any of Examples 92 to 96, comprising means for transitioning the HPM device from the initial operating mode to a second operating mode in response to an alert indicating a loss of the wireless link.

Example 98 is the apparatus of Example 97, the alert to comprise an alert of a Bluetooth Link Loss Service (LLS) service.

Example 99 is the apparatus of any of Examples 92 to 98, comprising means for transitioning the HPM device from the initial operating mode to a second operating mode in response to a determination that a transmit power of the HPR device is lower than a threshold value.

Example 100 is the apparatus of Example 99, the transmit power of the HPR device to be exposed by a Bluetooth Transmit Power Service (TPS) service.

Example 101 is the apparatus of any of Examples 92 to 100, comprising means for identifying the HPR device based on a received advertisement message.

Example 102 is the apparatus of any of Examples 92 to 101, comprising means for operating according to an HPM device role defined by a Bluetooth Low Energy (BLE) behavior profile.

Example 103 is the apparatus of Example 102, the BLE behavior profile to comprise a Proximity profile (PXP).

Example 104 is a system, comprising an apparatus according to any of Examples 92 to 103, and at least one radio frequency (RF) transceiver.

Example 105 is the system of Example 104, comprising at least one processor.

Example 106 is the system of any of Examples 104 to 105, comprising at least one RF antenna.

Example 107 is a wireless communication device, comprising a system according to any of Examples 104 to 106, and a display.

Example 108 is an apparatus, comprising means for performing a connection establishment procedure to establish a wireless link with a human proximity monitoring (HPM) device, means for generating heart rate information based on sensor data received from a heart rate sensor, and means for generating a human proximity report for transmission to the HPM device via the wireless link, the human proximity report to comprise the heart rate information.

Example 109 is the apparatus of Example 108, the sensor data to be exposed by a Bluetooth Heart Rate Service (HRS) service.

Example 110 is the apparatus of any of Examples 108 to 109, comprising means for exposing a current transmit power of the HPR device to the HPM device.

Example 111 is the apparatus of Example 110, the current transmit power of the HPR device to be exposed to the HPM device using a Bluetooth Transmit Power Service (TPS) service.

Example 112 is the apparatus of any of Examples 108 to 111, comprising means for operating according to an HPR device role defined by a Bluetooth Low Energy (BLE) behavior profile.

Example 113 is the apparatus of Example 112, the BLE behavior profile to comprise a Proximity profile (PXP).

Example 114 is the apparatus of any of Examples 108 to 113, comprising means for monitoring a status of the wireless link with the HPM device.

Example 115 is the apparatus of Example 114, comprising means for monitoring the status of the wireless link using a Bluetooth Link Loss Service (LLS) service.

Example 116 is the apparatus of any of Examples 108 to 115, comprising means for generating an advertisement message for transmission over a Bluetooth Low Energy (BLE) advertising channel.

Example 117 is the apparatus of Example 116, the advertisement message to comprise an identifier associated with the HPR device.

Example 118 is the apparatus of any of Examples 116 to 117, the advertisement message to comprise an indication of an availability of a human proximity reporting service.

Example 119 is a system, comprising an apparatus according to any of Examples 108 to 118, and at least one radio frequency (RF) transceiver.

Example 120 is the system of Example 119, comprising at least one processor.

Example 121 is the system of any of Examples 119 to 120, comprising at least one RF antenna.

Example 122 is a wearable wireless communication device, comprising a system according to any of Examples 119 to 121, and a display.

Example 123 is the wearable wireless communication device of Example 122, the display comprising a touch-screen display.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

It is emphasized that the Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate preferred embodiment. In the appended claims, the terms "including" and "in which" are used as the plain-English equivalents of the respective terms "comprising" and "wherein," respectively. Moreover, the terms "first," "second," and "third," etc. are used merely as labels, and are not intended to impose numerical requirements on their objects.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An apparatus, comprising:
    a memory; and
    logic, at least a portion of the logic comprised in circuitry coupled to the memory, the logic to:
        attempt to establish a wireless link with a human proximity reporting (HPR) device;
        determine whether the wireless link with the HPR device is established via a Bluetooth Link Loss Service (LLS);
        identify whether heart rate information is received from the HPR device via the wireless link exposed by a Bluetooth Heart Rate Service (HRS);
        determine an initial HPR state based on whether the wireless link is established and the heart rate information is received and indicates a detection of a human heart rate, the initial HPR state comprising one of a worn HPR device (HPRD) state and an unworn HPRD state; and
        select an initial operating mode for a feature of a human proximity monitoring (HPM) device based on the initial HPR state indicating whether the wireless link is established and the heart rate information is received and indicates a detection of the human heart rate, the initial operating mode comprising a human proximity trigger mode if the initial HPR state is the worn HPRD state and the initial operating mode comprising a timer trigger mode if the initial HPR state is the unworn HPRD state.

2. The apparatus of claim 1, the heart rate information to comprise a heart rate measurement.

3. The apparatus of claim 1, the feature to comprise an auto-lock feature.

4. The apparatus of claim 1, the logic to transition the HPM device from the initial operating mode to a second operating mode in response to an alert indicating a loss of the wireless link via the Bluetooth LLS.

5. The apparatus of claim 1, the logic to transition the HPM device from the initial operating mode to a second operating mode in response to a determination that a transmit power of the HPR device is lower than a threshold value.

6. A system, comprising:
    the apparatus of claim 1; and
    at least one radio frequency (RF) transceiver.

7. At least one non-transitory computer-readable storage medium comprising a set of instructions that, in response to being executed on a computing device, cause the computing device to:
    attempt to establish a wireless link with a human proximity reporting (HPR) device;
    determine whether the wireless link with the HPR device is established via a Bluetooth Link Loss Service (LLS);
    identify whether heart rate information is received from the HPR device via the wireless link exposed by a Bluetooth Heart Rate Service (HRS);
    determine an initial HPR state based on whether the wireless link is established and the heart rate information is received and indicates a detection of a human heart rate the initial HPR state comprising one of a worn HPR device (HPRD) state and an unworn HPRD state; and
    select an initial operating mode for a feature of a human proximity monitoring (HPM) device based on the initial HPR state indicating whether the wireless link is established and the heart rate information is received and indicates a detection of the human heart rate, the initial operating mode comprising a human proximity trigger mode if the initial HPR state is the worn HPRD state and the initial operating mode comprising a timer trigger mode if the initial HPR state is the unworn HPRD state.

8. The at least one non-transitory computer-readable storage medium of claim 7, the heart rate information to comprise a heart rate measurement.

9. The at least one non-transitory computer-readable storage medium of claim 7, the feature to comprise an auto-lock feature.

10. The at least one non-transitory computer-readable storage medium of claim 7, comprising instructions that, in response to being executed on the computing device, cause the computing device to transition the HPM device from the initial operating mode to a second operating mode in response to an alert indicating a loss of the wireless link via the Bluetooth LLS.

11. The at least one non-transitory computer-readable storage medium of claim 7, comprising instructions that, in response to being executed on the computing device, cause the computing device to transition the HPM device from the initial operating mode to a second operating mode in response to a determination that a transmit power of the HPR device is lower than a threshold value.

12. A computer-implemented method, comprising:
   attempting to establish a wireless link with a human proximity reporting (HPR) device;
   determining whether the wireless link with the HPR device is established via a Bluetooth Link Loss Service (LLS);
   identifying whether heart rate information is received from the HPR device via the wireless link exposed by a Bluetooth Heart Rate Service (HRS);
   determining an initial HPR state based on whether the wireless link is established and the heart rate information is received and indicates a detection of a human heart rate the initial HPR state comprising one of a worn HPR device (HPRD) state and an unworn HPRD state; and
   selecting an initial operating mode for a feature of a human proximity monitoring (HPM) device based on the initial HPR state indicating whether the wireless link is established and the heart rate information is received and indicates a detection of the human heart rate, the initial operating mode comprising a human proximity trigger mode if the initial HPR state is the worn HPRD state and the initial operating mode comprising a timer trigger mode if the initial HPR state is the unworn HPRD state.

13. The computer-implemented method of claim 12, wherein the heart rate information comprises a heart rate measurement.

14. The computer-implemented method of claim 12, wherein the feature comprises an auto-lock feature.

15. The computer-implemented method of claim 12, comprising transitioning the HPM device from the initial operating mode to a second operating mode in response to an alert indicating a loss of the wireless link via the Bluetooth LLS.

16. The computer-implemented method of claim 12, comprising transitioning the HPM device from the initial operating mode to a second operating mode in response to a determination that a transmit power of the HPR device is lower than a threshold value.

* * * * *